(12) United States Patent
Itoh et al.

(10) Patent No.: US 8,114,837 B2
(45) Date of Patent: Feb. 14, 2012

(54) METHOD FOR INHIBITING POSTPRANDIAL RISE IN BLOOD GLUCOSE BY ADMINISTERING κ-CASEIN

(75) Inventors: Yousuke Itoh, Yokohama (JP); Kouji Nomaguchi, Ebina (JP); Muneo Yamada, Yokosuka (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 12/704,723

(22) Filed: Feb. 12, 2010

(65) Prior Publication Data

US 2010/0144638 A1  Jun. 10, 2010

Related U.S. Application Data

(63) Continuation of application No. 12/088,276, filed as application No. PCT/JP2006/319551 on Sep. 29, 2006, now abandoned.

(30) Foreign Application Priority Data

Sep. 30, 2005  (JP) ................................. 2005-288338

(51) Int. Cl.
*A61K 38/00* (2006.01)
*A61P 3/10* (2006.01)
(52) U.S. Cl. .......................................... 514/6.8; 514/6.9
(58) Field of Classification Search ........................ None
See application file for complete search history.

(56) References Cited

U.S. PATENT DOCUMENTS

| 5,968,901 A | 10/1999 | Andersson et al. |
| 2004/0234666 A1 | 11/2004 | Law et al. |
| 2005/0148504 A1 | 7/2005 | Katunuma et al. |

FOREIGN PATENT DOCUMENTS

| EP | 1367065 A1 | 12/2003 |
| JP | 03-220130 A | 9/1991 |
| JP | 2004-521650 A | 7/2004 |
| JP | 2006-503099 A | 1/2006 |
| NZ | 285593 | 3/1999 |
| NZ | 333652 | 7/2000 |
| WO | 01/37850 A2 | 5/2001 |
| WO | 2004/034813 A2 | 4/2004 |

OTHER PUBLICATIONS

Mahe et al., Am. J. Clin. Nutr. 54: 534-538, 1991.*
Ghazzi et al., Cardiac and Glycemic Benefits of Troglitazone Treatment in NIDDM, Diabetes, 1997, vol. 46, pp. 433-439.
Wettergren et al., Truncated GLP-1 (Proglucagon 78-107-Amide) Inhibits Gastric and Pancreatic Functions in Man, Digestive Diseases and Sciences, 1993, vol. 38, No. 4, pp. 665-673.
Nauck et al., Normalization of fasting hyperglycaemia by exogenous glucagon-like peptide 1 (7-36 amide) in Type 2 (non-insulin-dependent) diabetic patients, Diabetologia, 1993, vol. 36, pp. 741-744.
Villanueva et al., Potent glycogenic effect of GLP-1 (7-36) amide in rat skeletal muscle, Diabetologia, 1994, vol. 37, pp. 1163-1166.
Drucker, Perspectives in Diabetes—Glucagon-Like Peptides, Diabetes, 1998, vol. 47, pp. 159-169.
European Patent Office, European Search Report in corresponding EP Application Serial No. 06798469.0-2405 issued on Oct. 8, 2009, 5 pages.
Hall et al., Casein and Whey Exert Different Effects on Plasma Amino Acid Profiles, Gastrointestinal Hormone Secretion and Appetite, British Journal of Nutrition (2003), vol. 89, pp. 239-248.
Herrmann et al., Glucagon-Like Peptide-1 and Glucose-Dependent Insulin-Releasing Polypeptide Plasma Levels in Response to Nutrients, Digestion (1995), vol. 56, pp. 117-126.
Examination Report issued in Counterpart New Zealand Patent Application No. 567046 on Jul. 2, 2010 (3 pages).

\* cited by examiner

*Primary Examiner* — Gyan Chandra
(74) *Attorney, Agent, or Firm* — Wood, Herron & Evans, LLP

(57) ABSTRACT

The invention relates to a GLP-1 secretagogue and an inhibitor of postprandial rise in blood glucose, containing κ-casein as an active ingredient, and a food or drink for promoting GLP-1 secretion and an inhibitory food or drink of postprandial rise in blood glucose, containing a milk-derived casein protein wherein κ-casein accounts for 60% by mass or more of the milk-derived casein.

5 Claims, 1 Drawing Sheet

METHOD FOR INHIBITING POSTPRANDIAL RISE IN BLOOD GLUCOSE BY ADMINISTERING κ-CASEIN

CROSS REFERENCE TO RELATED APPLICATIONS

This application is a Continuation of U.S. patent application Ser. No. 12/088,276 entitled "GLUCAGON-LIKE PEPTIDE-1 SECRETAGOGUE, GLUCAGON-LIKE PEPTIDE-1 SECRETAGOGUE FOOD OR DRINK, INHIBITOR OF POSTPRANDIAL RISE IN BLOOD GLUCOSE, AND INHIBITORY FOOD OR DRINK OF POSTPRANDIAL RISE IN BLOOD GLUCOSE" filed on Mar. 27, 2008 (pending), which is a 371 of International Patent Application Serial No. PCT/JP2006/319551 filed on Sep. 29, 2006, and also claims priority to Japanese Patent Application No. 2005-288388, filed on Sep. 30, 2005, the disclosures of which are hereby incorporated by reference herein.

TECHNICAL FIELD

The present invention relates to a glucagon-like peptide-1 secretagogue and a glucagon-like peptide-1 secretagogue food or drink, containing κ-casein as an active ingredient. Moreover, the present invention relates to an inhibitor of postprandial rise in blood glucose or an inhibitory food or drink of postprandial rise in blood glucose, containing κ-casein as an active ingredient.

BACKGROUND ART

Diabetes mellitus is one of the most typical metabolic diseases from which 200 million people are currently suffering in the world. The number of diabetic patients is predicted to exceed 300 million people in the year 2025, and is considered to be particularly increased in the South-East n region and the Western Pacific region where the entire populations are increasing. Also, in Japan, currently the diabetic population including patients on the borderline is considered to exceed 15 million people, and there is concern of further increase in the future.

Diabetes mellitus is largely classified into two types. Insulin-dependent diabetes mellitus (IDDM), referred to as type 1, is a disease in which pancreatic β cells are progressively destroyed by the immune system to cause a loss of insulin-producing cells, and this constitutes 5 to 10% of the entire diabetic population. Non-insulin-dependent diabetes mellitus (NIDDM), referred to as type 2, occurs as a result of defective responsiveness of tissues to insulin (insulin resistance) in the intake of glucose under the presence of a normal to high level of insulin, which also leads to the exhaustion of β cells. At present, type 2 diabetic patients constitutes 90 to 95% of the entire diabetic patients.

Currently, treatments such as insulin are performed against the dysfunction of β cells in the type 1 and the advanced-stage type 2 diabetes. However, there are problems in that the postprandial blood glucose level does not return to normal depending on the symptom, and the like. Moreover, the concerned treatments must be performed while avoiding hyperglycemia, hypoglycemia, metabolic acidosis, and ketosis, and need to be carefully programmed.

Furthermore, with respect to type 2 diabetes, treatments using drugs which promote the insulin production or secretion from the β cells, or drugs which improve the insulin resistance, are generally performed. However, these drugs promote the insulin production or secretion irrespective of the blood glucose level, and thus the blood glucose level should be controlled by diet so as not to fall into a hypoglycemic state or the like. There are also drawbacks of having side effects such as abdominal bloating, meteorism, increased flatulence, loose stools, diarrhea, and abdominal pain. Moreover, in cases of the insulin resistance improvers, it is reported that, as a result of the examination of their effects by hemoglobin Alc (HAlc) values or the like, the symptoms are not satisfactorily improved (Non-patent Document 1), and that side effects such as heart failure may possibly be induced by long term usage.

On the other hand, glucagon-like peptide-1 (GLP-1), a hormone secreted from L cells which are scattered in the gastrointestinal tract, is confirmed to have effects such as promoting a strong insulin secretion, stimulating the satiety center, and suppressing the gastrointestinal peristalsis, stimulated by food (Non-patent Document 2). These effects are all considered to be associated with inhibitory effects on rapid increase in the blood glucose level caused by food intake.

The effects of this GLP-1 stop working when the blood glucose level drops to 60 mg/dL or less, and thus it can be said that therapies using GLP-1 are more readily capable of controlling the blood glucose level as compared to conventional insulin therapies or the like (Non-patent Document 3). Further, GLP-1 has important functions such as an ability to promote the differentiation and proliferation of β cells to protect the pancreas, an ability to inhibit gluconeogenesis in the liver, an ability to improve the insulin resistance in cells, or an ability to improve peripheral glucose disposal (Non-patent Documents 4 and 5).

Therefore, many pharmaceutical manufacturers are dedicated to research with the expectation of a therapeutic effect of GLP-1 on type 2 diabetes. However, GLP-1 is extremely unstable in vivo, and thus it is required for example to optimize the administration method and the administration route, and to search for functional analogues which are highly stable in vivo. Practical implementation is still on the way at the present stage.

Therefore, research is being conducted not only on the direct administration of GLP-1 but also on the substances which promote the GLP-1 release in vivo, and naturally-derived components which have a GLP-1 release promoting effect are known.

For example, Patent Document 1 discloses that acid caseins and the like have a promoting effect on GLP-1 secretion. FIG. 1 of the Patent Document 1 shows results of the examination on the promoting effect on GLP-1 secretion by an in vitro test method. According to these, the promoting effect on GLP-1 secretion of acid caseins is approximately twice as compared to the control. Moreover, the promoting effect on GLP-1 secretion of acid-soluble proteins of casein micelles is approximately six times as compared to the control.

Moreover, Patent Document 2 discloses that a casein glycomacropeptide (CGMP) has a promoting effect on GLP-1 secretion. CGMP is a peptide obtained by cleaving the bond between phenylalanine 105 and methionine 106 of κ-casein with chymosin. FIG. 1 and FIG. 2 of Patent Document 2 show results of the examination on the promoting effect on GLP-1 secretion by an in vitro test method. According to them, the promoting effects on GLP-1 secretion of CGMP calcium salt and CGMP sodium salt are approximately twice to three times as compared to the control.

Since these components are naturally-derived and highly safe, it is expected that the administration thereof into diabetic patients including patients on the borderline can lead to the control of the postprandial blood glucose level without causing hypoglycemia.

(Patent Document 1) European Patent Application, Publication No. 1367065
(Patent Document 2) PCT International Publication No. WO 01/37850 Pamphlet
(Non-patent Document 1) Ghazzi et al., Diabetes, Vol. 46, No. 3, p. 433-439 (1997)
(Non-patent Document 2) Wettergren A, et al., Digestive Diseases and Sciences (Dig Dis Sci), Vol. 38, p. 665-673 (1993)
(Non-patent Document 3) Nauck et al., Diabetologia, Vol. 36, p. 741-744 (1993)
(Non-patent Document 4) M. L. Vellanueva et al., Diabetologia, Vol. 37, p. 1163 (1994)
(Non-patent Document 5) D. J. Drucker, Diabetes, Vol. 47, p. 159 (1998)

DISCLOSURE OF INVENTION

Problems to be Solved by the Invention

However, components described in Patent Documents 1 and 2 have only two to three times higher, at most approximately six times higher promoting effect on GLP-1 secretions, as compared to the control. A large amount of these components must be consumed to obtain a certain degree of effect. According to Patent Document 2, the preferable dose of CGMP should desirably be 5 to 10 g per 100 g of food.

Moreover, the acid-soluble proteins of casein micelles described in Patent Document 1 are proteins obtained such that a whey is removed from milk through to obtain casein micelles, and then these casein micelles are dissolved with an acid. Only a very small amount of these proteins can be obtained from milk. Although the promoting effect on GLP-1 secretion thereof is about six times as compared to the control and is slightly higher than that of acid caseins, it is difficult to produce a necessary amount for practical use.

Accordingly, various types of naturally-derived components having the GLP-1 release promoting effect are known, but all are poor in practicability.

The present invention addresses the abovementioned problems with an object of providing a GLP-1 secretagogue and an inhibitor of postprandial rise in blood glucose which have a high promoting effect on GLP-1 secretion and therefore a high inhibitory effect on postprandial rise in blood glucose, and are practically capable of providing a sufficient amount of an active ingredient, with use of a safe and naturally-derived component.

Moreover, another object is to provide a food or drink for promoting GLP-1 secretion and an inhibitory food or drink of postprandial rise in blood glucose which have a high promoting effect on GLP-1 secretion and therefore a high inhibitory effect on postprandial rise in blood glucose, and are capable of mass production as a food or drink.

Means for Solving the Problems

In order to achieve the abovementioned objects, the present invention employs the following constructions.
(1) A glucagon-like peptide-1 secretagogue, containing κ-casein as an active ingredient.
(2) A glucagon-like peptide-1 secretagogue food or drink, containing a casein protein derived from milk (milk-derived casein protein), wherein κ-casein accounts for 60% by mass or more of the milk-derived casein protein.
(3) The glucagon-like peptide-1 secretagogue food or drink according to (2), further containing a carbohydrate.
(4) An inhibitor of postprandial rise in blood glucose, containing κ-casein as an active ingredient.
(5) An inhibitory food or drink of postprandial rise in blood glucose, containing a milk-derived casein protein, wherein κ-casein accounts for 60% by mass or more of the milk-derived casein protein.
(6) The inhibitory food or drink of postprandial rise in blood glucose according to (5), further containing a carbohydrate.

EFFECTS OF THE INVENTION

The GLP-1 secretagogue of the present invention contains κ-casein being a milk component as an active ingredient, and thus is highly safe. Moreover, since the promoting effect on GLP-1 secretion is extremely high and a large amount of κ-casein serving as the active ingredient can be obtained, the practicability is high.

Since the food or drink for promoting GLP-1 secretion of the present invention contains κ-casein being a milk component at a higher ratio as compared to normal milk, the promoting effect on GLP-1 secretion is extremely high. Moreover, since mass production is possible, the practicability is high. Furthermore, since the κ-casein by itself serves as a nutrient, the food or drink is excellent as a medical diet for diabetic patients who need to take nutrients while controlling the blood glucose level.

The inhibitor of postprandial rise in blood glucose of the present invention contains κ-casein being a milk component as an active ingredient, and thus is highly safe. Moreover, the blood glucose level is suppressed by the promoting effect on GLP-1 secretion of κ-casein, and thus hypoglycemia is not induced. Furthermore, since the inhibitory effect on postprandial rise in blood glucose is extremely high and a large amount of κ-casein serving as the active ingredient can be obtained, the practicability is high.

Since the inhibitory food or drink of postprandial rise in blood glucose of the present invention contains κ-casein being a milk component at a much higher ratio as compared to normal milk, the inhibitory effect on postprandial rise in blood glucose is extremely high. Moreover, the blood glucose level is suppressed by the promoting effect on GLP-1 secretion of κ-casein, and thus hypoglycemia is not induced. Moreover, since mass production is possible, the practicability is high. Furthermore, since the κ-casein by itself serves as a nutrient, the food or drink is excellent as a medical diet for diabetic patients who need to take nutrients while controlling the blood glucose level.

BEST MODE FOR CARRYING OUT THE INVENTION

Figure 1:
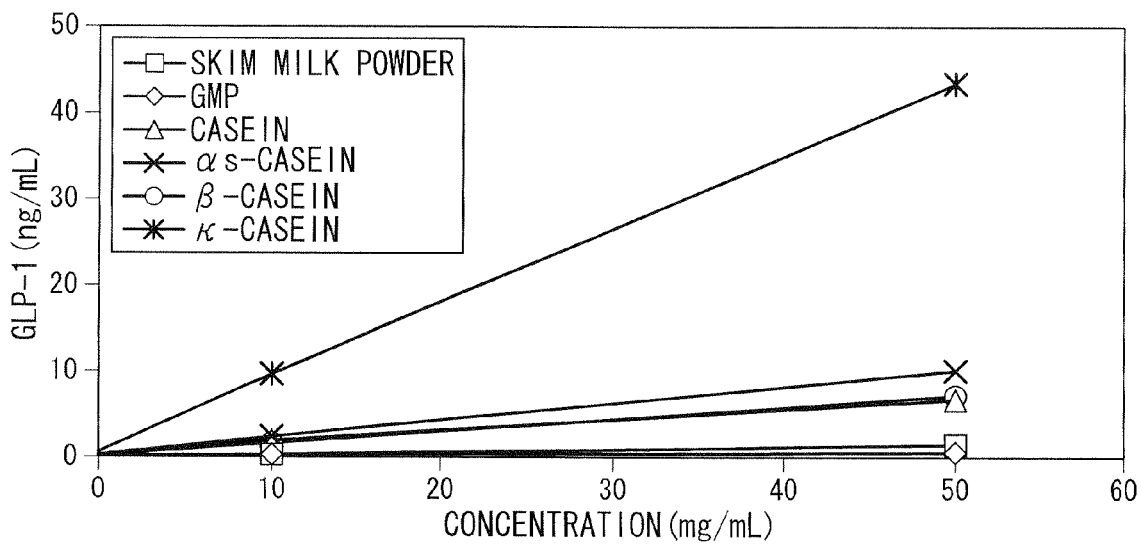
FIG. 1 is a graph showing test results of Test Example 1.

Preferred embodiments of the present invention will be explained in more detail. However, the present invention is not to be limited to the following preferred embodiments, and may be freely modified within the scope of the present invention.
(GLP-1 Secretagogue)
The GLP-1 secretagogue of the present invention contains κ-casein as an active ingredient. In the present invention, the phrase "contains κ-casein as an active ingredient" means to contain an effective amount of κ-casein capable of providing an intended effect (a promoting effect on GLP-1 secretion in the case of the GLP-1 secretagogue, or an inhibitory effect on postprandial rise in blood glucose in the case of an inhibitor of postprandial rise in blood glucose that will be described later). Moreover, in the present invention, the phrase "promoting GLP-1 secretion" means to promote the secretion of GLP-1 by cells that have a GLP-1 secretional capacity.

κ-casein is a protein contained in milk. That is to say, milk proteins are present in casein micelles and whey, and are classified into caseins and whey proteins. When skim milk obtained by removing fat from milk is added with an acid at 20° C. to adjust to pH 4.6, the precipitated part is casein and proteins contained in the supernatant liquid are whey proteins.

Casein is further fractioned into αs-casein, β-casein, κ-casein, and a small amount of γ-casein. κ-casein is one of the most rapidly migrating casein components (α-casein) in the moving boundary electrophoresis that is soluble with 0.4M $CaCl_2$ (4° C., pH 7.0). κ-casein is easily soluble with water as compared to αs-casein and β-casein, and thus is easy to handle for use as a food ingredient, κ-casein accounts for about 10% by mass of milk proteins.

κ-casein differs from CGMP which is a decomposition product of κ-casein.

κ-casein can be purified from raw milk, skim milk, casein, sodium caseinate, acid casein, or the like through well-known steps such as centrifugal separation, pH adjustment with an acid, and addition of urea, sulfuric acid, or calcium.

For example, a cream phase is removed from raw milk through centrifugal separation to obtain skim milk, and then the pH is adjusted to 4.6 so as to precipitate caseins. Then, the whey fraction is removed through centrifugal separation to obtain the casein fraction. Next, the separated casein fraction is redissolved at pH 8.0, and then is added with calcium chloride, followed by the removal of a generated precipitation through centrifugal separation and collection of the supernatant. This supernatant is subjected to dialysis and subsequent freeze-drying to thereby obtain proteins having κ-casein as a main component.

For use in oral intake, the calcium precipitation method is preferably used. For use as a food ingredient, highly purified κ-casein is preferably used for facilitating the adjustment of the addition amount.

The present inventors have found that κ-casein has an extremely high promoting effect on GLP-1 secretion. GLP-1 is a hormone secreted from L cells which are scattered in the gastrointestinal tract and has effects of promoting strong insulin secretion, stimulating the satiety center, suppressing the gastrointestinal peristalsis, and so forth. These effects are all associated with inhibitory effects on rapid increase in the blood glucose level caused by food intake. Moreover, the effects of this GLP-1 stop working when the blood glucose level drops to 60 mg/dL or less, and thus therapies by promoting the GLP-1 secretion are safer and more readily capable of controlling the blood glucose level, as compared to conventional insulin therapies or the like.

Further, GLP-1 has important abilities such as an ability of promoting the differentiation and proliferation of β cells to protect the pancreas, an ability of inhibiting gluconeogenesis in the liver, an ability of improving the insulin resistance in cells, or an ability of improving peripheral glucose disposal. These effects are all associated with inhibitory effects on rapid increase in the blood glucose level caused by food intake. Therefore, GLP-1 is effective for the prevention or the treatment of diabetes.

The GLP-1 secretagogue of the present invention may be, for example, a medical composition, or may be a component to be added to a food or drink.

In the case of a medical composition, administration thereof can be performed into a human or an animal orally, through tubes, or enterally, for example. Various dosage forms being forms of general medical formulations can be selected in accordance with these administration methods and the purpose of the treatment. Representative examples thereof may include a tablet, a pill, a powder, a liquid formulation, a suspension, an emulsion, granules, and a capsule.

There is no specific limitation on the additive which can be used for preparing formulations, and additives that are generally used for medical compositions such as an excipient, a binder, a disintegrator, a lubricant, a stabilizer, a flavoring agent, a diluent, and a solvent for injection may be used.

Examples of the excipient include: sugar derivatives such as lactose, white sugar, glucose, mannitol, and sorbitol; starch derivatives such as corn starch, potato starch, α-starch, dextrin, and carboxymethyl starch; cellulose derivatives such as crystalline cellulose, hydroxypropylcellulose, hydroxypropylmethylcellulose, carboxymethylcellulose, and carboxymethylcellulose calcium; Arabian gum; dextran; pullulan; silicate derivatives such as light anhydrous silicic acid, synthetic aluminum silicate, and magnesium aluminometasilicate; phosphate derivatives such as calcium phosphate; carbonate derivatives such as calcium carbonate; and sulfate derivatives such as calcium sulfate.

Examples of the binder include, in addition to the above excipients: gelatin; polyvinylpyrrolidone; and macrogol.

Examples of the disintegrator include, in addition to the above excipients: chemically modified starch or cellulose derivatives such as croscarmellose sodium, sodium carboxymethyl starch, and crosslinked polyvinylpyrrolidone.

Examples of the lubricant include: talc; stearic acid; metal stearates such as calcium stearate and magnesium stearate; colloidal silica; waxes such as VEEGUM and spermaceti; boric acid; glycol; carboxylic acids such as fumaric acid and adipic acid; sodium carboxylates such as sodium benzoate; sulfates such as sodium sulphate; leucine; lauryl sulfates such as sodium lauryl sulfate and magnesium lauryl sulfate; silicic acids such as anhydrous silicic acid and silicic acid hydrate; and starch derivatives.

Examples of the stabilizer include: parahydroxybenzoate esters such as methylparaben and propylparaben; alcohols such as chlorobutanol, benzyl alcohol, and phenylethyl alcohol; benzalkonium chloride; acetic anhydride; and sorbic acid.

Examples of the flavoring agent include sweeteners, acidifiers, and perfumes. Examples of the solvent for injection include water, ethanol, and glycerin.

The GLP-1 secretagogue of the present invention may be contained in a food or drink so as to make a food or drink for promoting GLP-1 secretion. The form of the GLP-1 secretagogue to be contained in a food or drink is not specifically limited, and may solely consist of proteins having κ-casein as a main component, or may contain another ingredient which is permitted to be contained in a food or drink, in addition to κ-casein.

The effective dose of the GLP-1 secretagogue of the present invention varies depending on the degree of the diabetic symptom, the age of the patient, and so forth in the case of the oral administration (which is also the same in the case of the addition to a food or drink), although 5 to 500 mg/kg/day is preferable, and 25 to 150 mg/kg/day is more preferable as the amount of the active ingredient (κ-casein).

(Food or Drink for Promoting GLP-1 Secretion)

The food or drink for promoting GLP-1 secretion of the present invention contains a milk-derived casein protein, wherein κ-casein accounts for 60% by mass or more of the milk-derived casein protein. In dairy products containing normal milk or a milk-derived casein protein, the proportion of κ-casein in the casein protein is about 13% by mass.

On the other hand, since the food or drink for promoting GLP-1 secretion of the present invention contains a lot of κ-casein at 60% by mass or more, the food or drink can be used as an active ingredient to demonstrate similar effects to those of the GLP-1 secretagogue.

There is no specific limitation on the κ-casein content in the food or drink for promoting GLP-1 secretion of the present invention. Preferably, κ-casein is contained at an amount to a degree which allows a reasonable intake of the abovementioned dose for the effective GLP-1 secretion promotion per day, and normally, κ-casein is contained at an amount of 0.05 to 2.5% by mass.

For example, if a patient weighing 50 kg takes a food or drink for promoting GLP-1 secretion which contains 1.5 g of κ-casein in 100 g of the food or drink, the dose would be 30 mg/kg. This is comparable to the preferable effective dose of the GLP-1 secretagogue per day, and is capable of demonstrating similar effects to those of the GLP-1 secretagogue, at an amount allowing a reasonable intake as a food or drink.

Moreover, since the κ-casein by itself serves as a nutrient, the above food or drink is suitable for a medical diet or an nutrition food, for diabetic patients who need to take nutrients while controlling the blood glucose level, and functional foods (, food for special dietary use such as foods for patients, and food for health).

The food or drink for promoting GLP-1 secretion of the present invention may be produced using, as raw materials, the GLP-1 secretagogue and other ingredients which are permitted to be contained in a food or drink, or may be produced by formulating the GLP-1 secretagogue of the present invention in an already-known food or drink containing other ingredients.

Regarding other ingredients to be contained in the food or drink for promoting GLP-1 secretion, any ingredient which is approved for use for foods/drinks by food regulations such as may be used without any specific limitations so long as the promoting effect on GLP-1 secretion is not deteriorated. For example, carbohydrates such as dextrin and starch; proteins such as gelatin, a soybean protein, and a corn protein; amino acids such as alanine, glutamine, and isoleucine; polysaccharides such as cellulose and Arabian gum; and oils and fats such as soybean oil and medium chain triglyceride, may be contained. In particular, if a carbohydrate is contained, the effect of the present invention is of great significance since it enables the intake of nutrients while controlling the blood glucose level.

The form of the food or drink for promoting GLP-1 secretion is not specifically limited. Examples thereof include: drinks such as coffee, tea, soft drinks, carbonated drinks, nutrient drinks, fruit drinks, lactic acid drinks (including concentrated stock solutions and powders for preparation of these drinks); frozen desserts such as ice cream, and chipped ice; noodles such as buckwheat noodle, Japanese wheat noodle, Chinese, Chinese dumpling wrap, Chinese shao mai skins, Chinese noodle, and instant noodle; confectioneries such as sweet drops, chewing gum, candies, gum, chocolate, sweet tablets, snack food, biscuits, jelly, jam, cream, and baked confectioneries; processed foods of seafood/meat such as, ham, and sausage; dairy products such as processed milk and fermented milk; oils and fats and processed foods thereof such as salad oil, oil for deep fry, margarine, mayonnaise, shortening, whipped cream, and dressing; seasonings such as sauce and gravy; and soups, stews, salads, delicatessens, pickles, and bread.

The food or drink for promoting GLP-1 secretion of the present invention is preferably labeled with the usage instruction showing the purpose of GLP-1 secretion promotion. Specifically, for example, the food or drink is preferably marketed as "a food or drink for promoting GLP-1 secretion which contains κ-casein as an active ingredient".

Here, the term "label" means all manners for informing consumers about the above usage instruction, and any label which suggests or implies the above usage instruction may fall under the "label" of the present invention irrespective of the purpose of the label, the content of the label, the type of the object/media of the label, and the like. Examples thereof include acts of indicating the above usage instruction on goods according to the food or drink for promoting GLP-1 secretion of the present invention or casings thereof, acts of assigning, delivering, display for the purpose of assignment or delivery, importing, or providing through an electronic telecommunication line of such goods or casings thereof having the indication of the above usage instruction, acts of displaying or circulating a goods-related advertisement, price list, or trade document having the indication of the above usage instruction, or providing information on such contents having the indication of the above usage instruction through an electromagnetic method (such as the Internet).

Preferable labels are labels approved by the government or the like (for example, labels approved on the basis of various constitutions established by the government and executed in a form on the basis of such an approval), and particularly labels on casings, packages, catalogs, pamphlets, promotional materials for on-site sales such as POP, or other documents are preferable.

Moreover, examples thereof also include labels as food for health, functional food, enteral nutrition food, food for special dietary use, nutrient functional food, and quasi drugs, and other labels approved by the, such as food for specified health use and labels approved by like constitutions. Examples of the latter labels include labels as food for specified health use, labels as food for specified health use, labels indicating that the body structure and function are affected, labels indicating a decrease in the risk of disease. More in detail, labels as food for specified health use regulated by of (Apr. 30, 2003, No. 86 of the, of Japan) (in particular, labels of the usage instruction for health care) and like labels can be enumerated as typical examples.

Phrases and words used for such labels are not limited to the terms of "for promoting glucagon-like peptide-1 secretion" and "for promoting GLP-1 secretion" only but may be any other terms which indicate the promoting effect on GLP-1 secretion.

(Inhibitor of Postprandial Rise in Blood Glucose)

The inhibitor of postprandial rise in blood glucose of the present invention contains κ-casein as an active ingredient, and has a similar construction to that of the GLP-1 secretagogue of the present invention. As described above, GLP-1 has an inhibitory effect on postprandial rise in blood glucose. Accordingly, the inhibitor of postprandial rise in blood glucose of the present invention which contains κ-casein having a high promoting effect on GLP-1 secretion as an active ingredient, has a high inhibitory effect on postprandial rise in blood glucose.

Moreover, as described above, GLP-1 is safe and readily capable of controlling the blood glucose level. Furthermore, GLP-1 has various abilities associated with the inhibitory effects on rapid increase in the blood glucose level caused by food intake. Therefore, GLP-1 is effective for the prevention or the treatment of diabetes.

Accordingly, the inhibitor of postprandial rise in blood glucose of the present invention based on the promoting effect on GLP-1 secretion is useful for the prevention or the treatment of diabetes.

(Inhibitory Food or Drink of Postprandial Rise in Blood Glucose)

The inhibitory food or drink of postprandial rise in blood glucose of the present invention contains a milk-derived casein protein, wherein κ-casein accounts for 60% by mass or more of the milk-derived casein protein. Moreover, if a carbohydrate is further contained, the effect of the present invention is of great significance since it enables the intake of nutrients while controlling the blood glucose level. The inhibitory food or drink of postprandial rise in blood glucose of the present invention has a similar construction to that of the food or drink for promoting GLP-1 secretion of the present invention.

Since the inhibitory food or drink of postprandial rise in blood glucose of the present invention contains a lot of κ-casein at 60% by mass or more as an active ingredient thereof, the food or drink exhibits similar effects to those of the inhibitor of postprandial rise in blood glucose.

Similarly to the food or drink for promoting GLP-1 secretion mentioned above, the inhibitory food or drink of postprandial rise in blood glucose of the present invention is preferably labeled with the usage instruction showing the purpose of inhibiting postprandial rise in blood glucose. Specifically, for example, the food or drink is preferably marketed as "an inhibitory food or drink of postprandial rise in blood glucose which contains κ-casein as an active ingredient".

Phrases and words used for such labels are not limited to terms "for inhibiting postprandial rise in blood glucose" only but may be any other term which indicates the inhibitory effect on postprandial rise in blood glucose.

EXAMPLES

Test Example 1

1. Preparation of Test Samples

Skim milk powder (manufactured by Morinaga Milk Industry CO., LTD.), a glycomacropeptide (manufactured by Arla Foods Ingredients amba, GMP), casein (manufactured by Fonterra Co-operative Group Ltd., Alacid 720), αs-casein (manufactured by Sigma-Aldrich Corp., purity of 70% by mass), β-casein (manufactured by Sigma-Aldrich Corp., purity of 90% by mass), and κ-casein (manufactured by Sigma-Aldrich Corp., purity of 80% by mass) were each dissolved in Krebs-Ringer-HEPES buffer to prepare test samples at a concentration of 10 mg/mL or 50 mg/mL as the total protein content. Krebs-Ringer-HEPES buffer was used as a control.

2. Preparation of Differentiated Human Gastrointestinal-Derived Cell Line

A human gastrointestinal-derived cell line NCI-H716 (CCL-251) was purchased from American Type Culture Collection (ATCC). The purchased cell line was cultured in an RPMI1640 medium (manufactured by Sigma-Aldrich Corp., R8758) in which 10 mM HEPES buffer (manufactured by Sigma-Aldrich Corp., H0887), 1 mM sodium pyruvate (manufactured by Sigma-Aldrich Corp., S8636), 13.9 mM glucose, 10% by volume of fetal bovine serum, 100 U/mL penicillin, and 100 μg/mL streptomycin (manufactured by Invitrogen Corporation., 15140-122) are formulated at each final concentrations, at 37° C. in an atmosphere with 5% by volume of carbon dioxide.

The cultured cell line was collected through centrifugal separation, and was resuspended into a DMEM medium (manufactured by Sigma-Aldrich Corp.) containing 10% by volume of fetal bovine serum at its final concentration, at $1.0 \times 10^6$ cells/mL. Then, the cell suspension was aliquoted at 250 μL for each plate of which the surface was treated with a matrigel manufactured by Becton, Dickinson and Company, and was further cultured at 37° C. in an atmosphere with 5% by volume of carbon dioxide for 2 days, to allow differentiation into a cell line having the GLP-1 secretional capacity.

3. Measurement of Promoting Effect on GLP-1 Secretion

The culture solution of the differentiated human gastrointestinal-derived cell line that had been prepared in step 2, was replaced with 250 μL of the test sample that had been prepared in step 1, followed by culturing at 37° C. in an atmosphere with 5% by volume of carbon dioxide for 2 hours. Then, the culture supernatant was collected through centrifugal separation, and was added with a protease inhibitor cocktail (manufactured by Nacalai Tesque, Inc.). The resultant mixture was preserved at −80° C. until measurement.

The sample that had been preserved at −80° C. was thawed. Then, the concentration of GLP-1 secreted in the culture supernatant was measured. The GLP-1 concentration was measured using the Glucagon-Like-Peptide-1 (GLP-1) (7-36) EIA kit (manufactured by Phoenix Pharmaceuticals, Inc.).

4. Test Results

Test results (a test was performed three times for each sample) are shown in Table 1 and FIG. 1. In Table 1, "versus control" means a ratio to 0.055 that is the average value of the measured results of the control. The standard deviation of the control was 0.012 ng/mL.

As shown in Table 1, κ-casein showed a 175 times promoting effect on GLP-1 secretion at the concentration of 10 mg/mL and a 789 times effect at the concentration of 50 mg/mL, with respect to the control. As shown in FIG. 1, these values are remarkably higher as compared to casein and other fraction components in casein (αs-casein and β-casein). The present test revealed that κ-casein has a remarkably high promoting effect on GLP-1 secretion.

TABLE 1

|  | 10 mg/mL | | | 50 mg/mL | | |
| --- | --- | --- | --- | --- | --- | --- |
|  | Average value (ng/mL) | Standard deviation (ng/mL) | Versus control | Average value (ng/mL) | Standard deviation (ng/mL) | Versus control |
| Skim milk powder | 0.304 | 0.045 | 5.53 | 1.51 | 0.210 | 27.5 |
| GMP | 0.265 | 0.043 | 4.82 | 0.573 | 0.130 | 10.1 |
| Casein | 1.94 | 0.300 | 35.3 | 6.75 | 0.890 | 123 |
| αs-casein | 2.41 | 0.380 | 43.9 | 10.1 | 1.60 | 184 |
| β-casein | 1.64 | 0.140 | 29.9 | 7.21 | 0.900 | 131 |
| κ-casein | 9.63 | 1.00 | 175 | 43.4 | 4.90 | 789 |

Test Example 2

1. Test Methods

Eighteen commercially available mice weighing 31 to 33 g (Slc: ddy, provided from Japan SLC, Inc., 7-week-old male) were fed for 14 days, and then no food was given for the following 20 hours. Then, the weight and the blood glucose level were measured, and the mice were divided into two groups: a κ-casein administration group; and a control group so that the respective groups had equivalent average weights and blood glucose levels.

Then, the mice of the κ-casein administration group were forcibly and orally administered with a test liquid having 25 mg of κ-casein and 2000 mg of soluble starch per kg of body weight which were liquefied with sterile distilled water. Meanwhile, the mice of the control group were forcibly and orally administered with a test liquid having 2000 mg of soluble starch per kg of body weight which were liquefied with sterile distilled water.

Blood was collected from these mice through the caudal vein at every 30 minutes from the preadministration of the test liquid until 120 minutes postadministration, and the blood glucose level (blood glucose level (mg/dL)) was respectively measured using the blood glucose self-monitoring system "One Touch Ultra" (manufactured by Johnson & Johnson K.K.).

2. Test Results

Table 2 shows the body weights of No. 1 to 9 mice of the control group at the preadministration of the test liquid, and the measured results of their blood glucose levels (mg/dL) at every 30 minutes from the preadministration of the test liquid (0 min) until 120 minutes postadministration (120 min). The average values and the standard deviations of these body weights and respective blood glucose levels are also shown.

Moreover, Table 3 shows the body weights of No. 1 to 9 mice of the κ-casein administration group at the preadministration of the test liquid, and the measured results of their blood glucose levels (mg/dL) at every 30 minutes from the preadministration of the test liquid (0 min) until 120 minutes postadministration (120 min). The average values and the standard deviations of these body weights and respective blood glucose levels are also shown.

TABLE 2

| Control group | Body weight (g) | 0 min (mg/dL) | 30 min (mg/dL) | 60 min (mg/dL) | 90 min (mg/dL) | 120 min (mg/dL) |
|---|---|---|---|---|---|---|
| 1 | 38.4 | 80 | 238 | 212 | 181 | 148 |
| 2 | 39.3 | 71 | 192 | 189 | 142 | 108 |
| 3 | 36.6 | 75 | 229 | 208 | 156 | 126 |
| 4 | 33.7 | 74 | 196 | 156 | 145 | 124 |
| 5 | 39.2 | 95 | 237 | 202 | 170 | 127 |
| 6 | 38.5 | 66 | 242 | 218 | 188 | 155 |
| 7 | 41.1 | 82 | 225 | 183 | 130 | 116 |
| 8 | 43.1 | 104 | 237 | 219 | 181 | 169 |
| 9 | 38.8 | 86 | 222 | 206 | 169 | 135 |
| Average | 38.7 | 81.4 | 224 | 199 | 162 | 134 |
| Standard deviation | 2.63 | 12.0 | 18.4 | 20.2 | 20.2 | 19.6 |

TABLE 3

| κ-casein administration group | Body weight (g) | 0 min (mg/dL) | 30 min (mg/dL) | 60 min (mg/dL) | 90 min (mg/dL) | 120 min (mg/dL) |
|---|---|---|---|---|---|---|
| 1 | 41.7 | 85 | 201 | 202 | 168 | 132 |
| 2 | 38.9 | 74 | 175 | 159 | 121 | 91 |
| 3 | 38.6 | 93 | 208 | 182 | 151 | 116 |
| 4 | 35.9 | 65 | 178 | 182 | 143 | 72 |
| 5 | 40.0 | 69 | 179 | 170 | 129 | 102 |
| 6 | 33.9 | 70 | 152 | 123 | 98 | 67 |
| 7 | 37.6 | 89 | 207 | 176 | 148 | 124 |
| 8 | 41.7 | 102 | 226 | 200 | 154 | 114 |
| 9 | 37.9 | 88 | 182 | 167 | 124 | 99 |
| Average | 38.5 | 81.7 | 190 | 173 | 137 | 102 |
| Standard deviation | 2.55 | 12.6 | 22.4 | 23.7 | 21.2 | 22.3 |

Figure 2:
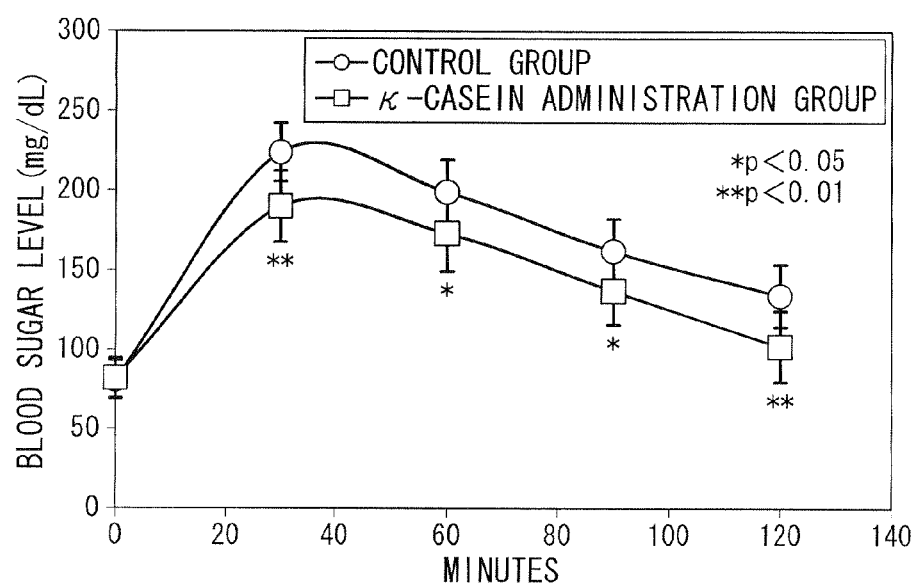
FIG. 2 is a graph showing test results of Test Example 2.

Moreover, FIG. 2 shows the average values of the blood glucose levels shown in Table 2 and Table 3 plotted with respect to time after the administration of the test liquid. The respective horizontal bars indicate the mean values±standard deviations.

The significant difference between the κ-casein administration group and the control group was judged by t-test. In FIG. 2, the mark * indicates a significant difference at p<0.05 and the mark ** indicates a significant difference at p<0.01.

As shown in FIG. 2, the κ-casein administration group was confirmed to significantly inhibit the increase in blood glucose level as compared to the control group, at all points of 30, 60, 90, and 120 mins postadministration.

From the above results, it was revealed that postprandial rise in blood glucose can be inhibited by the intake of κ-casein.

Separately, the promoting effect on GLP-1 secretion of respective samples was also measured at each time point, and thereby it was confirmed to be correlated with the values of the inhibitory effect on postprandial rise in blood glucose.

Next is a further detailed description of the present invention with reference to Examples, but the present invention is not to be construed as being limited to these Examples.

Example 1

14 kg of commercially available casein (Alacid 720: manufactured by Fonterra Co-operative Group Ltd.,) was added to 77 kg of distilled water, which was dissolved by adjusting to pH 8.0 with a 5.0 mass/volume % sodium hydroxide aqueous solution. Next, a 40 mass/volume % calcium chloride aqueous solution was added thereto at the final concentration of 300 mM, and the mixture was sterilized by heating at 85° C. for 10 minutes. The resultant solution was left standing for 1 hour, followed by centrifugal separation at 5000 g. The supernatant was collected and was subjected to ultrafiltration and subsequent freeze-drying, to obtain about 900 g of a purified product of κ-casein.

The obtained purified product was dissolved in a distilled water, and the purity was confirmed through SDS-PAGE and using the Zone Densitometry apparatus (ATTO'S Densitometry Software produced by ATTO Corporation), which showed that the purity of κ-casein was 60% by mass or more.

The obtained κ-casein was filled with 2.0 g for each gelatin capsules No. 1 listed in the pharmacopeia of Japan (Aliment Industry Co. Ltd.). The joint of the cap and the body of the capsule was sealed with a gelatin to produce an inhibitor of rise in blood glucose containing κ-casein as an active ingredient.

Example 2

Commercially available κ-casein (manufactured by Sigma-Aldrich Corp., purity of 80% by mass) was used to produce a food having the composition shown in Table 4.

TABLE 4

| (Liquid food) | Blending amount (g) |
|---|---|
| κ-casein | 0.7 |
| Dextrin | 13.8 |
| Vegetable oil | 2.9 |
| Granulated sugar | 0.5 |
| Soybean protein | 3.3 |
| Cellulose | 0.4 |
| pH adjuster | 0.3 |
| Magnesium chloride | 0.05 |
| Emulsifier | 0.1 |
| Perfume | 0.1 |
| Thickening stabilizer | 0.01 |
| Total (dissolved in distilled water) | 100 mL |

INDUSTRIAL APPLICABILITY

The GLP-1 secretagogue of the present invention contains κ-casein being a milk component as an active ingredient, and thus is highly safe. Moreover, since the promoting effect on GLP-1 secretion is extremely high and a large amount of κ-casein serving as the active ingredient can be obtained, the practicability is high.

Since the food or drink for promoting GLP-1 secretion of the present invention contains κ-casein being a milk component at an extremely high ratio as compared to normal milk, the promoting effect on GLP-1 secretion is extremely high. Moreover, since mass production is possible, the practicability is high. Furthermore, since the κ-casein by itself serves as a nutrient, the food or drink is excellent as a medical diet for diabetic patients who need to take nutrients while controlling the blood glucose level.

The inhibitor of postprandial rise in blood glucose of the present invention contains κ-casein being a milk component as an active ingredient, and thus is highly safe. Moreover, the blood glucose level is suppressed by the promoting effect on GLP-1 secretion of κ-casein, and thus hypoglycemia is not induced. Furthermore, since the inhibitory effect on postprandial rise in blood glucose is extremely high and a large amount of κ-casein serving as the active ingredient can be obtained, the practicability is high.

Since the inhibitory food or drink of postprandial rise in blood glucose of the present invention contains κ-casein being a milk component at an extremely high ratio as compared to a normal milk, the inhibitory effect on postprandial rise in blood glucose is extremely high. Moreover, the blood glucose level is suppressed by the promoting effect on GLP-1 secretion of κ-casein, and thus hypoglycemia is not induced. Moreover, since mass production is possible, the practicability is high. Furthermore, since the κ-casein by itself serves as a nutrient, the food or drink is excellent as a medical diet for diabetic patients who need to take nutrients while controlling the blood glucose level.

What is claimed is:

1. A method for inhibiting postprandial rise in blood glucose, comprising administering purified κ-casein to a subject in need thereof in an amount effective to inhibit postprandial rise in blood glucose in said subject, wherein purity of κ-casein is 60% by mass or more.

2. The method according to claim 1, wherein the amount effective to inhibit postprandial rise in blood glucose is from 5 to 500 mg/kg/day as the amount of κ-casein.

3. The method according to claim 1, wherein the amount effective to inhibit postprandial rise in blood glucose is from 25 to 150 mg/kg/day as the amount of κ-casein.

4. The method according to claim 1, wherein purity of the purified κ-casein is 80% by mass.

5. The method according to claim 1, wherein the subject is a human or an animal.

* * * * *